(12) United States Patent
Stogniew et al.

(10) Patent No.: US 6,814,987 B2
(45) Date of Patent: Nov. 9, 2004

(54) COMPOSITIONS AND METHODS OF USE FOR EXTRACTS OF MAGNOLIACEAE PLANTS

(75) Inventors: Martin Stogniew, Blue Bell, PA (US); Walter Chambliss, Memphis, TN (US); Robert Garrison, Jr., Carlsbad, CA (US)

(73) Assignee: NPI, LLC., Irvine, CA (US)

( * ) Notice: Subject to any disclaimer, the term of this patent is extended or adjusted under 35 U.S.C. 154(b) by 8 days.

(21) Appl. No.: 10/423,506

(22) Filed: Apr. 25, 2003

(65) Prior Publication Data

US 2003/0206975 A1 Nov. 6, 2003

Related U.S. Application Data

(62) Division of application No. 09/996,254, filed on Nov. 29, 2001, now Pat. No. 6,582,735.
(60) Provisional application No. 60/255,402, filed on Dec. 15, 2000.

(51) Int. Cl.[7] .............................................. A61K 35/78
(52) U.S. Cl. ...................................... 424/769; 424/725
(58) Field of Search ................................ 424/725, 769

(56) References Cited

U.S. PATENT DOCUMENTS

| | | | | |
|---|---|---|---|---|
| 4,537,996 | A | 8/1985 | Kooda et al. ............... | 568/442 |
| 5,447,719 | A | 9/1995 | Kamataki | |
| 5,589,182 | A | 12/1996 | Tashiro et al. | |
| 5,869,540 | A * | 2/1999 | Smith ......................... | 514/783 |
| 6,004,969 | A * | 12/1999 | Hu ............................ | 514/282 |
| 6,193,977 | B1 | 2/2001 | Han et al. | |
| 6,210,680 | B1 * | 4/2001 | Jia et al. .................... | 424/725 |
| 6,358,540 | B1 * | 3/2002 | Ozog et al. ................. | 424/725 |
| 2002/0025348 | A1 | 2/2002 | Basu et al. | |
| 2002/0061339 | A1 * | 5/2002 | Stogniew et al. ........... | 424/725 |

FOREIGN PATENT DOCUMENTS

| | | | |
|---|---|---|---|
| CN | 1105557 | | 7/1995 |
| JP | 59122414 | | 7/1984 |
| JP | 59130811 | * | 7/1984 |
| JP | 60042485 | | 3/1985 |
| JP | 61005024 | | 1/1986 |
| JP | 01102007 | | 4/1989 |
| JP | 03098562 | | 4/1991 |
| JP | 03123734 | | 5/1991 |
| JP | 404154728 | * | 5/1992 |
| JP | 04108736 | | 8/1992 |
| JP | 08-003033 | | 9/1996 |
| JP | 10017485 | | 1/1998 |
| JP | 1003627 | | 2/1998 |
| JP | 10194984 | | 7/1998 |
| JP | 10-338631 | | 12/1998 |
| JP | 200229869 | | 8/2000 |

OTHER PUBLICATIONS

Watanabe, K. Watanabe, H.Y.; Tamamoto, N; Yoshizaki, M.; "Studies on the Active Principles of Magnolia Bark, Centrally Acting Muscle Relaxant Activity of Magnolol and Honokiol." Japanese Journal of Pharmacology.

Watanabe, K. ; Watanabe, H.; Goto, Y.; Yamaguchi, M.; Yamaguchi, M.; Yamamoto, N.; Hagino, K. "Pharmacological Properties of Magnolol and Honokiol Extracted from Magnolia Officinalis Central Depressant Effects," Journal of Medicinal Plant Research Plant Medica. 49, pp. 130–106. (1983).

Tang W, Eisenbrand G, Chinese Drugs of Plant Origin, Springer Verlag. Berlin. (1992).

Vanherweghem J ; Depierreux M; Tielemans C ; Abramowicz, D; Dratwa, M; Jadoul, M.; Richard, C.; Vandervelde, D., Verbeelen, D.; Vanhaelen–Fastre, R.; Vanhaelem, M., "Rapidly progressive interstital renal fibrosis in young women: association with slimming regimen including Chinese Herbs," The Lancet. 341, 8842, pp. 8842, pp. 387–391. (1993).

Maruyama, Y; Kuribara, H.; Morita, M.; Yuzurihara, M.; Weintraub, S. T.; "Identification of Magnolol and Honokiol as Anxiolytic Agents in Extracts of Saiboku–to, an oriental Herbal Medicine," Journal of Natural Products, 61; 135–18 (1998).

Chevalier, A., The Encyclopedia of Medicinal Plants, Dorling Kinderslay, London. (1995).

MT Hsieh, FY Chueh and MT Lin, "Magnolol Decreases Body Temperature by Reducing 5–Hydroxtryptamine Release in the Rat Hypothalamus"Clinical and Experimental Pharmacology and Physiology, vol. 25, No. 10, pp. 813–817. Oct. 1998.

Kuribare, H.; Stavinoha, W.B.; and Maruyama, Y.; "Honokiol, a putative Anxiolytic Agent Extracted from Magnolia Bark. has no Diazeparn–like Side–effects in Mice," Journal of Pharmaceutical Pharmacology, 51, 97–103 (1999).

Yuji Maruyama and Hisashi Kuribara. "Overview of the Pharmacological Features of Honokiol." CNS Drug Reviews, vol. 6, No. 1, pp. 35–44, Apr. 2000.

(List continued on next page.)

Primary Examiner—Christopher R. Tate
(74) Attorney, Agent, or Firm—Stetina Brunda Garred & Brucker

(57) ABSTRACT

The invention relates to compositions and methods for preventing, treating, or managing sleeplessness, restlessness, weight gain including weight gain due to stress or lack of sleep, or all three comprising the administration of a prophylactically and therapeutically effective amount of Magnoliaceae plant or extracts thereof to a mammal in need of such therapy. Preferably the mammal is human and the compositions have comprise at least two compounds selected from magnolol, honokiol, and magnoflorine. Alternatively, the compositions may also comprise about 2% honokiol by weight of the composition.

19 Claims, No Drawings

OTHER PUBLICATIONS

Eitchi Techikawa, Masabumi Takahashi and Takeshi Kashimoto. "Effects of Extract and Ingredients Isolated from Magnolia obovata Thunberg on Catecholamine Secretion from Bovine Adrenal Chromaffin Cells" Biochemical Pharmacology, vol. 60, pp. 443–440. Aug. 2000.

Talpur, N.A., Echard, B.W.; Manohar, V; and Preuss, H.G.; "Influence of a combination of herbs on appetite suppression and weight loss in rats," Diabetes, Obesity & Metabolism, 3. 3 (2001).

Brown M.; Bing, C. King, P.; Pickavance L; Heal, D.; and Wilding, J.; "Sibutramine reduces feeding, body fat, and improves insulin resistance in dietary–obese male winstar rats independently of hypothalamic neuropeptide Y," British Journal of Pharmacology. 138. 8 (2001).

Database WPI, Derwent Publications Ltd., London, GB; AN 1999–114788, XP002210436 & JP 10 338631 A (Tsumura and Co), Dec. 22, 1998, abstract.

* cited by examiner

COMPOSITIONS AND METHODS OF USE FOR EXTRACTS OF MAGNOLIACEAE PLANTS

This application is a Divisional application of application Ser. No. 09/996,254, filed Nov. 29, 2001, which issued as U.S. Patent No. 6,582,735.

This application claims the benefit of U.S. Provisional Application No. 60/255,402 filed Dec. 15, 2000, which is incorporated by reference herein in its entirety.

1. INTRODUCTION

The present invention relates to novel methods and compositions for the treatment, prevention, or management of sleeplessness, restlessness and weight gain. The methods and compositions utilize plants, portions thereof or extracts therefrom belonging to the *Magnoliaceae* family. In addition, the methods and compositions utilize mixtures of specific small molecules extracted from the plants belonging to the family *Magnoliaceae*, such as, but not limited to, magnolol, honokiol, and magnoflorine. The unique compositions of the invention may also comprise various amounts of the *Magnoliaceae* plant, plant extract, plant extracts combined with different amounts of biologically active small molecules or other therapeutic agents. These compositions are particularly useful for the treatment of sleeplessness, restlessness and weight gain in humans. The invention also encompasses various modes of administration of the therapeutic extracts or other compositions of the invention.

2. BACKGROUND OF THE INVENTION

The recent growth in sales of natural products labeled as dietary supplements in the United States has renewed scientific interest in the study of the prophylactic and therapeutic effects of multi-component botanical products. Unlike single entity pharmaceutical products, botanical products comprise a large number of diverse chemical constituents that often act synergistically to exert a desired biological effect. The type of extraction process utilized and the manner in which the formulation is standardized have dramatic effects on the pharmacological activity of the final product. The development of new botanical products requires multidisciplinary effort consisting of expertise in ethnobotany, natural product chemistry, analytical chemistry, pharmacology, and natural product extraction.

2.1 Sleeplessness, Restlessness and Weight Control

Sleep is necessary for survival and good health, but why sleep is needed or exactly how it benefits people is not fully understood. Individual requirements for sleep vary widely; healthy adults may need as few as 4 hours or as many as 9 hours of sleep every day. Most people sleep at night, but many must sleep during the day to accommodate work schedules. This situation often leads to sleep disorders. Most sleep disorders are common.

How long a person sleeps and how rested a person feels on waking can be influenced by may factors, including excitement or emotional distress. Medications also can play a part; some medications make a person sleepy while other makes sleeping difficult. Even some food elements of additives such as caffeine, strong spices, and monosodium glutamate (MSG) may affect sleep.

Sleep is not a uniform state; it has several distinct stages through which it normally cycles five or six times every night. Sleep progresses from stage 1 (the lightest level, during which the sleeper can be awakened easily) to stage 4 (the deepest level, during which waking the sleeper is difficult). In stage 4, the muscles are relaxed, the blood pressure is at the lowest, and the heart and breathing rates are at their slowest. Besides these four stages, there is a form of sleep accompanied by rapid eye movements (REM) and behavioral activity. During REM sleep, electrical activity in the brain is unusually high, somewhat resembling that of wakefulness. The eye movement and brain wave changes that accompany REM sleep can be recorded electrically on an electroencephalogram (EEG).

In REM sleep, the rate and depth of breathing increase, but the muscles are greatly relaxed more so than during the deepest levels of non-REM sleep. Most dreaming occurs during REM and stage 3 sleep, while most talking during sleep, night terrors, and sleepwalking occur during stages 3 and 4. During a normal night's sleep, REM sleep immediately follows each of the five or six cycles of four-stage non-REM sleep, but it can occur at any of the stages.

If emotional stress is causing the sleep disorder, treatment to relieve the stress is more useful than taking sleep medication. When the sleep disorder is cause by depression, the depression should be thoroughly evaluated and treated by a doctor. Some antidepressant drugs can improve sleep because they have sedating properties. When sleep disorders interfere with a person's normal activities and sense of well-being, the intermittent use of sleep medications (sedatives, hypnotics) may be useful.

A sedative drug decreases activity, moderates excitement, and calms the recipient, whereas a hypnotic drug produces drowsiness and facilitates the onset and maintenance of a state of sleep that resembles natural sleep in its electroencephalographic characteristics and from which the recipient can be aroused easily. The latter effect sometimes is called hypnosis.

Nonbenozodiazepine sedative-hypnotic drugs belong to a group of agents that depress the central nervous system (CNS) in a relative nonselective, dose-dependent fashion, producing progressively calming or drowsiness (sedation), sleep (pharmacological hypnosis), unconsciousness, coma, surgical anesthesia, and fatal depression of respiration and cardiovascular regulation.

Hypnotics (sedatives, minor tranquilizers, anti-anxiety drugs) are among the most commonly used drugs. Most are quite safe, but all can lose their effectiveness once a person becomes accustomed to them. An undesirable side effect of hypnotics, however, are the withdrawal symptoms when use is discontinued. After more than a few days' use, discontinuing a hypnotic can make the original sleep problem worse (rebound insomnia) and increase anxiety. Also most hypnotics require a doctor's prescription because they may be habit-forming or addictive, and overdose is possible. Hypnotics are particularly risky for the elderly and for people with breathing problems because they tend to suppress brain areas that control breathing. They also reduce daytime alertness, making driving or operating machinery hazardous. Hypnotics are especially dangerous when taken with alcohol, other hypnotics, narcotics, antihistamines, and anti-depressants. All of these drugs cause drowsiness and can suppress breathing, making the combined effects more dangerous.

Stress plays a major role in weight management. Stress activates the hypothalamic/pituitary/adrenal axis resulting in an increase in cortisol levels. Cortisol increases the availability of glucose through hepatic gluconeogeneses and the release of glucose substrates from fat cells and muscles. The uptake of glucose is inhibited, resulting in hyperglycemia and hyperlipidemia. The increase in cortisol levels signals the brain that the body is in stress causing food cravings, especially high fat, high sugar foods. These foods, in turn, cause additional stress thereby fueling the stress-cortisol cycle. Eventually, more fat is stored than the body needs unless sufficient exercise is in place to compensate, or the stress is reduced. Central nervous stimulants have been used to suppress appetite in an attempt to counteract stress-induced appetite. This approach not only aggravates the problem due to a direct CNS stimulation effect, but also has a high abuse potential and several serious side effects including cardiovascular and cerebral vascular effects. Ephedra, which is also known as ma huang, is a dietary supplement that is used for weight control and is an example of this type of approach. The purported mechanism of action for Ephedra is CNS stimulation due to the presence of ephedrine alkaloids in the extract.

2.3 *Magnoliaceae* Plant Extracts

Extracts from plants belonging to the family *Magnoliaceae* have been and may still be used in Chinese herbalism. The bark of *Magnolia officinalis* Rehder et Wilson, "Hou-po" in Chinese, has been used in Chinese traditional medicine. (Watanabe, K.; Watanabe, H. Y.; Goto, Y.; Yamamoto, N.; Yoshizaki, M.; "Studies on the Active Principles of *Magnolia* Bark. Centrally acting Muscle Relaxant Activity of Magnolol and Honokiol," *Japan. J. Pharmacol.* 25, 605 (1975)). Magnolol is the bioactive constituent of *Magnolia* Cortex, the bark of *Magnolia officinalis*, Rehd. Et Wils., *Magnoliaceae* or of *M. obvata*, Thunb., called wakoboku in Japanese medicine. Honokiol is the bioactive principle isolated from the bark of *Magnolia obovata*, Thunb., *Magnoliaceae* and other *Magnolia* species used in Japanese and Chinese traditional medicine.

The bark of *Magnolia officinalis*, is reportedly used as an antibacterial, antiseptic, antispasmodic, aphrodisiac, appetizer, digestive, diuretic, emmenagogue, expectorant, ophthalmic, stomachic, and tonic. (Chevalier, A., *The Encyclopedia of Medicinal Plants*, Dorling Kindersley, London, 1995).

The ether extract of magnolia bark showed a central depressant effect and centrally acting muscle relaxation effect. (Watanabe et al.) Muscle relaxation was shown to be dose-dependent, wherein minimum effective doses required at least 90–100 mg/kg, while sedative symptoms were observed at lower doses. At large doses, honokiol showed a muscle relaxing effect for 3 hours (250 mg/kg) and produced a loss of righting reflex (500 mg/kg). (Watanabe et al. p. 606).

In mice, magnolol produced hypomotility, ptosis, and sedation at 63 mg/kg when administered intraperitoneally. (Watanabe, K.; Watanabe, H.; Goto, Y.; Yamaguchi, M.; Yamamoto, N.; Hagino, K., "Pharmacological Properties of Magnolol and Honokiol Extracted from *Magnolia* officinalis: Central Depressant Effects," *Journal of Medicinal Plant Research: Planta Medica*, 49, pp. 130–108, (1983)). At a dose of 125 mg/kg magnolol induced sedation, ataxia, and prominent muscle relaxation for 2 hr after injection. Magnolol at a dose of 250 mg/kg produced an ataxia within 10 min, loss of righting reflex in 40 min, and muscle relaxation over 3 hr. Honokiol produced similar effects at doses of 125, 250, and 500 mg/kg i.p. Id.

To date, there are a number of sleep disorders for which there is no dietary supplement available to either prevent or alleviate the disorder or symptoms associated therewith. It is desirable to discover and develop dietary supplements or pharmaceutical compositions based upon natural materials that are both safe and effective. It is particularly desirable to develop plant extracts for the prevention, treatment, or control of sleeplessness, restlessness and weight gain do to stress or lack of sleep.

3. SUMMARY OF THE INVENTION

The invention described herein encompasses compositions and methods of treating or preventing sleeplessness, restlessness or weight gain including, but not limited to, weight gain due to stress or lack of sleep. The methods comprise the administration of a therapeutically or prophylactically effective amount of an extract from the *Magnoliaceae* family, particularly to a human in need of such therapy. The plants belonging to the *Magnoliaceae* family include, but are not limited to, plants belonging to the genus *Liriodendron* and *Magnolia*. Species belonging to the *Liriodendron* genus include *Liriodendron tulipifera* and *Liriodendron chinense*. Species belonging to the *Magnolia* genus include, but are not limited to, *Magnolia acuminata, Magnolia ashei, Magnolia biodii, Magnolia cylindrica, Magnolia cambellii, Magnolia denudata, Magnolia fraseri, Magnolia grandiflora, Magnolia hypoleuca, Magnolia kobus, Magnolia liliiflora, Magnolia loegneri, Magnolia macrophylla, Magnolia officinalis, Magnolia pyramidata, Magnolia sargentiana, Magnolia seiboldii, Magnolia soulangiana, Magnolia sprengeri, Magnolia stellata, Magnolia tripetala, Magnolia virginiana, Magnolia zenii,* and *Michelia figo.* The extracts of the invention are prepared using solvents such as lower alcohols, water, and mixtures thereof.

Preferably, the compositions comprise *Magnoliaceae* plant extracts soluble in a lower alcohol, water, and mixtures thereof, or at least two compounds selected from the group consisting of magnolol, honokiol, and magnoflorine. More preferably, the compositions comprise about 2% of honokiol by weight. The compositions may contain a pharmaceutically acceptable carrier, excipient, or diluent. The compositions can be included as unit dosage suitable for parenteral, oral, or intravenous administration to a human. Alternatively, the compositions are dietary supplements, food compositions or beverage compositions suitable for human or animal consumption.

The *Magnoliaceae* plant extract is obtained by cutting or pulverizing a plant of the family *Magnoliaceae*, extracting the cut or powdered plant parts with a suitable aqueous solvent for a time sufficient to form an extract. Subsequently, the extract is concentrated under reduced pressure and optionally dried. Further, the extract may optionally be purified to remove undesirable components.

The methods described herein comprise methods for treating, preventing, and managing sleeplessness, restlessness, or both by administering a therapeutically effective amount of a plant extract or a composition comprising a *Magnoliaceae* plant or plant extract, wherein the *Magnoliaceae* plant belongs to the genus *Liriodendron* or *Magnolia*. The method of treating the above mentioned conditions includes administering an extract obtained using a solvent selected from the group consisting of a lower alcohol, water, and mixtures thereof. Alternatively, the extract comprises at least two compounds selected from the group consisting of magnolol, honokiol, magnoflorine and pharmaceutically acceptable salts thereof. Preferably, the extracts or compositions thereof comprise at least 2% honokiol by weight, and more preferably 2% honokiol.

3.1 Definitions

As used herein, unless otherwise specified, the term "*Magnoliaceae* plant" includes, but is not limited to, any part of a plant within the family *Magnoliaceae*. The plant parts may include plant bodies preferably the stalk, leaves, fruit or rind, bark, flowers, stems, roots, or seeds. Preferred plants within the *Magnoliaceae* family are discussed below.

As used herein, unless otherwise specified, the term "treating sleeplessness" or "treatment of sleeplessness" includes, but is not limited to, preventing or reducing the disturbances in falling asleep, staying asleep, duration of sleep, or abnormal sleep behaviors.

As used herein, unless otherwise specified, the term "treating restlessness", "treatment of restlessness" or "preventing restlessness" includes, but is not limited to, causing to rest or relax preferably without inducing sedation or hypnosis, inducing relaxation without inducing muscle relaxation, and relieving nervous tension or stress. Thus, the invention also encompasses methods of inducing relaxation without reduction or loss of motor function in humans.

As used herein, unless otherwise specified, the term "managing weight gain" includes, but is not limited to, treating, preventing or reducing weight gain, suppressing appetite and in a preferred embodiment treating, preventing or reducing weight gain associated with stress or lack of sleep.

As used herein, unless otherwise specified, the term "physiologically acceptable carrier," includes, but is not limited to, a carrier medium that does not interfere with the effectiveness of the biological activity of any active ingredients, is chemically inert, and is not toxic to the consumer or patient to whom it is administered.

As used herein, unless otherwise specified, the term "pharmaceutically acceptable salts" refers to salts prepared from pharmaceutically acceptable non-toxic acids and bases, including inorganic and organic acids and bases.

As used herein, unless otherwise specified, the term "preventing," includes, but is not limited to, inhibition or the averting of symptoms associated with a particular disease or disorder.

As used herein, unless otherwise specified, the term "treating" refers to the administration of the composition after the onset of symptoms of the disease or disorder whereas "preventing" refers to the administration prior to the onset of the symptoms, particularly to patients at risk of the disease or disorder.

As used herein, unless otherwise specified, the term "lower alcohol" includes, but is not limited to, straight chained or branched, substituted or unsubstituted hydrocarbon compounds having at least one hydroxyl group and having one to five carbon atoms. Lower alcohols include, but are not limited to, methanol, ethanol, n-propanol, isopropanol, butanols, and mixtures thereof.

As used herein, unless otherwise specified, the term "obese" includes, but is not limited to, a person having a Body Mass Index (B MI) of greater than or equal to about 26.

As used herein, unless otherwise specified, the term "average weight" or "of average weight" includes, but is not limited to, a person having a Body Mass Index (BMI) of less than about 26.

4. DETAILED DESCRIPTION OF THE INVENTION

The invention encompasses methods for preventing, treating, and managing sleeplessness, restlessness, or weight gain including, but not limited to, weight gain due to lack of sleep comprising the administration of a prophylactically and therapeutically effective amount of *Magnoliaceae* plant or an extract thereof to a mammal in need of such therapy. In a preferred embodiment, the mammal is human and the extracts comprise at least two compounds selected from the group consisting of magnolol, honokiol, and magnoflorine. In a more preferred embodiment, the extracts comprise at least 2% honokiol by weight of the composition and preferably, 2% honokiol by weight of the composition. In a most preferred embodiment the extracts are aqueous or lower alcohol aqueous extracts.

The invention further encompasses compositions for preventing, treating, and managing sleeplessness, restlessness, or weight gain including, but not limited to, weight gain due to lack of sleep comprising a therapeutically effective amount of *Magnoliaceae* plant or an extract thereof including, but not limited to, magnolol, honokiol and magnoflorine.

In one embodiment of the invention, the composition for preventing sleeplessness comprises *Magnoliaceae* plant or extracts thereof in an amount sufficient to prevent the onset of sleeplessness or sleeplessness related symptoms. In another embodiment of the invention, for mammals already suffering from sleeplessness, the invention is directed to compositions and administered dosages comprising *Magnoliaceae* plant in sufficient amount to reduce sleeplessness or the symptoms associated with sleeplessness. In yet another embodiment of the invention, for mammals already suffering from sleeplessness, the invention is directed to a method for treating sleeplessness by . administering compositions comprising *Magnoliaceae* plant extract in a therapeutically sufficient amount to treat sleeplessness.

In another embodiment of the invention, the composition for reducing or preventing restlessness comprises *Magnoliaceae* plant or extracts thereof in an amount sufficient to prevent the onset of restlessness or restlessness related symptoms. In another embodiment of the invention, the composition for treating restlessness is in sufficient amount and regularly administered dosage to reduce or eliminate restlessness related symptoms in mammals suffering from restlessness. In yet another embodiment of the invention, for mammals already suffering from restlessness, the invention is directed to a method for treating restlessness by administering compositions containing *Magnoliaceae* plant extract in a therapeutically sufficient amount to either prevent or treat restlessness.

In yet another embodiment, the invention encompasses compositions, including pharmaceutical compositions or dietary supplements, to be used in managing weight gain including, but not limited to, weight gain due to stress or lack of sleep. Further, the invention encompasses methods for managing weight gain in a mammal which comprises administering a magnoliaceae plant or extract thereof to a mammal in need thereof.

In another embodiment, the invention encompasses methods for managing weight gain in a human, particularly wherein said human is an obese male or an obese female.

In a further embodiment, the invention encompasses methods for managing weight gain in a human, particularly wherein said human is a male or a female of average weight.

In still another embodiment, the invention encompasses methods for managing weight gain in a human, particularly wherein said human is not concurrently using; has not previously used another dietary supplement or pharmaceutical composition for weight control; or both. The extracts of the invention are particularly useful for humans taking prescription medications for weight gain including, but not limited to, weight gain due to stress or lack of sleep. The invention, however, encompasses the use of the extracts in humans before, during, and after treatment with prescription therapies.

More preferably, the *Magnoliaceae* plant extract is obtained by extracting *Magnoliaceae* plant parts with a lower alcohol, water, or mixtures thereof. In another preferred embodiment of the invention, the compositions comprise a *Magnoliaceae* plant or an extract thereof and an additional amount of magnolol, honokiol, or magnoflorine in excess to any amount that may be present in the *Magnoliaceae* plant extract.

The invention encompasses compositions which comprise magnolol, honokiol, magnoflorine, or pharmaceutically acceptable salts thereof and pharmaceutically acceptable excipients, carriers, or diluents. Further, such magnolol, honokiol, magnoflorine compositions can comprise non-sedating sleep aids or other therapeutic agents. The compositions comprise magnolol, honokiol, magnoflorine, or a mixture thereof in an amount sufficient and regularly administered dosage to prevent, treat, or manage sleeplessness, restlessness, weight gain due to stress or lack of sleep, or all three.

The disclosure is based, in part, on the discovery that *Magnoliaceae* plant or extracts thereof, alone or in combination with other sleep aids, induces relaxation without loss of motor function and restful sleep. Without being limited by theory, it is believed that *Magnoliaceae* plant extracts act synergistically or at least more than additively by binding to one or more receptor sites to collectively diminish the symptoms of sleeplessness or restlessness without causing a sedative or addictive effect.

In a preferred embodiment, the invention encompasses compositions, and the use thereof, which comprises a water-soluble extract of a *Magnoliaceae* plant. In a most preferred embodiment, such extracts are produced by extraction with an aqueous alcohol solvent system such that the extracts preferably comprise one or more of the following small organic compounds which naturally occur in the plants: magnolol, honokiol, magnoflorine, and the like. It has been discovered that such extracts have a unique receptor binding affinities despite the fact that the extracts are mixtures of components. Thus, the extracts of the invention have unique benefits in preventing, treating, or managing disorders. Moreover, the preferred extracts of the invention are useful for treating and preventing sleeplessness, restlessness, weight gain due to stress or lack of sleep, or all three without a sedative or addictive effect. Similarly, the extracts of the invention reduce or avoid adverse effects associated with certain CNS drugs such as physical dependency, withdrawal problems, impaired coordination, loss or reduction of motor function, slowed reaction time, sedation, weight gain, constipation, dry mouth, confusion, blurred vision, nausea, diarrhea, or headaches.

The extracts of the invention are particularly useful for humans taking prescription medications for sleeplessness, restlessness, or both. The invention, however, encompasses the use of the extracts in humans before, during, and after treatment with prescription or conventional therapies.

In accordance with the present invention, the *Magnoliaceae* plant can be used alone or in combination with other known therapeutic agents or techniques to reduce sleeplessness, restlessness, weight gain due to stress or lack of sleep, or all three. Such agents may include vitamins and minerals, such as magnesium, calcium, or non-sedating sleep aids.

Since novel formulations of *Magnoliaceae* plant are disclosed herein, the invention also encompasses methods of using the novel formulations for the treatment of sleeplessness, restlessness, weight gain due to stress or lack of sleep, or all three in a mammal, wherein the mammal is preferably a human.

4.1 Method for Obtaining *Magnoliaceae* Plant Extracts

The plants belonging to the "*Magnoliaceae* family" used in the present invention are plants belonging to the genus *Liriodendron* and *Magnolia*. Species belonging to the *Liriodendron* genus include, but are not limited to, *Liriodendron tulipifera* and *Liriodendron chinense*. Species belonging to the *Magnolia* genus include, but are not limited to, *Magnolia acuminata, Magnolia ashei, Magnolia biodii, Magnolia cylindrica, Magnolia cambellii, Magnolia denudata, Magnolia fraseri, Magnolia grandiflora, Magnolia hypoleuca, Magnolia kobus, Magnolia liliiflora, Magnolia loegneri, Magnolia macrophylla, Magnolia officinalis, Magnolia pyramidata, Magnolia sargentiana, Magnolia seiboldii, Magnolia soulangiana, Magnolia sprengeri, Magnolia stellata, Magnolia tripetala, Magnolia virginiana, Magnolia zenii,* and *Michelia figo*. The most preferable plants are *Magnolia officinalis* and its variants.

The *Magnoliaceae* plant includes the plant parts as defined above, optionally the plant parts may be cut into small pieces or ground into a powder. Preferably, the plant part includes an extract of the *Magnoliaceae* plant. During a typical extraction process, the *Magnoliaceae* plant body, preferably cut into small pieces or ground into a powder, is placed in a Soxhlet extractor and extracted with any suitable solvent. Typical solvents include, but are not limited to, water, lower alcohols, or mixtures thereof. Preferably, the solvents used in the extraction include water, ethanol, and mixtures thereof. The solvent is maintained at reflux and the *Magnoliaceae* plant body is extracted for about 8 hours to about 48 hours. Preferably, the *Magnoliaceae* plant is extracted for about 12 hours to about 40 hours, and more preferably for about 18 hours to about 30 hours.

Subsequently, the solvent is separated and reduced in volume. Optionally, the solvent may be extracted with a second solvent. Thereafter, the extraction solvents are collected and reduced in volume either under low pressure or by evaporation to form a residue. Optionally, the residue is diluted and purified by gravity chromatography using at least one suitable solvent easily determined by a skilled artisan with little or no experimentation as the mobile phase. Optionally, the ratio of solvents within the solvent mixture may be gradually changed.

An alternative extraction process comprises adding a suitable solvent to the *Magnoliaceae* plant body, either grounded into a powder or cut into pieces. The solvents include, but are not limited to water, a lower alcohol, and mixtures thereof. Preferably, the solvents are water, ethanol, or mixtures thereof. The mixture of *Magnoliaceae* plant and solvent is allowed to sit overnight, preferably for about 6 hours to about 40 hours, preferably for about 8 hours to about 18 hours. Subsequently, the mixture is filtered, separating the solids from the filtrate. The solids are mixed with more solvent and allowed to sit overnight, preferably for about 6 hours to about 40 hours, preferably from about 12 hours to 32 hours, and more preferably from about 8 hours to about 18 hours. The mixture is separated a second time by filtration and the filtrates from both extractions are combined, and concentrated under reduced pressure to obtain a residue. The residue is vacuum dried for about 1 to about 10 hours, preferably for about 1 to about 2 hours at room temperature.

Yet another alternative extraction process comprises combining a suitable solvent to the *Magnoliaceae* plant body, either grounded into a powder or cut into pieces, in a ratio of about 4:1 to about 7:1 by volume to form a mixture. The mixture is heated to a temperature of about 1° F. below the boiling point of the solvent and stirred for about an hour. Preferably, if water is used as a solvent, the temperature is about 212° F. The mixture is filtered and the filtrate is washed with fresh solvent in a volume ratio of about 1:1. Subsequently the filtrate is concentrated under reduced volume and dried in a vacuum oven. In this method, suitable solvents include ethanol, methanol, chlorinated solvents, propanol, 2-propanol, water, denatured industrial grade alcohol such as SDA-35, and mixtures thereof. Preferably, suitable solvents include water, ethanol, SDA-35, and mixtures thereof.

4.2 Compositions Comprising *Magnoliaceae* Plant Extracts and Modes of Administration The invention comprises compositions of *Magnoliaceae* plant or plant extracts with physiologically suitable carriers including, but not limited to, pharmaceutical carriers for the treatment of sleeplessness, restlessness, weight gain including, but not limited to, weight gain due to stress or lack of sleep, or all three. In a preferred embodiment, the compositions of the present invention comprise at least two compounds selected from the group consisting of magnolol, honokiol, and magnoflorine. More preferably, the compositions include at least 2% honokiol by weight of the composition; preferably including 2% honokiol by weight of the composition. Most preferably, the compositions are obtained from the extraction of *Magnoliaceae* plant parts with an aqueous organic solution mixture, in particular a water and ethanol solution mixture, comprising small molecule compounds.

The magnitude of the therapeutic dose of an active ingredient in the acute or chronic management of a disorder or condition will vary with the severity of the disorder or condition to be treated and the route of administration. The dose, and perhaps the dose frequency, will also vary according to age, body weight, response, and the past medical history of the consumer or patient. Suitable dosing regimens can be readily selected by those skilled in the art with due consideration of such factors.

In one embodiment of the present invention, *Magnoliaceae* plant comprises about 2% to about 100% by weight of the composition. In a preferred embodiment, *Magnoliaceae* plant comprises about 5% to about 95% by weight of the composition. In a more preferred embodiment, *Magnoliaceae* plant comprises about 10% to about 90% by weight of the composition.

In another embodiment of the present invention using *Magnoliaceae* plant extracts, *Magnoliaceae* plant extracts comprise about 25% to about 100% by weight of the composition. In a preferred embodiment, *Magnoliaceae* plant extracts comprise about 35% to about 90% by weight of the composition. In a more preferred embodiment, *Magnoliaceae* plant extracts comprise about 40% to about 80% by weight of the composition.

In an embodiment, the composition of the invention comprises *Magnoliaceae* plant or plant extract present in an amount of about 35% to about 90% by weight and at least one non-sedating sleep aid. Alternatively, the compositions of the invention can be administered sequentially or simultaneously in combination with at least one non-sedating sleep aid.

*Magnoliaceae* plant or extracts thereof can be formulated using standard formulation techniques into gel caps, teas, tablets, etc. See, e.g., *Remington's Pharmaceutical Sciences*, 18th ed., Mack Publishing, Easton Pa. (1990). *Magnoliaceae* plant extracts of the invention may be formulated into a dietary supplement or a pharmaceutical preparation for the administration to mammals for the treatment of sleeplessness, restlessness, weight gain, preferably weight gain due to stress or lack of sleep, or all three. In a preferred embodiment, the mammal is human.

Compositions comprising *Magnoliaceae* plant extracts of the invention formulated in a compatible pharmaceutical carrier may be prepared, packaged, and labeled for treatment, prevention, or management of sleeplessness, restlessness, or symptoms thereof.

If the composition is water-soluble, then it may be formulated in an appropriate buffer, for example, phosphate buffered saline or other physiologically compatible solutions. Alternatively, if the resulting composition has poor solubility in aqueous solvents, then it may be formulated with a non-ionic surfactant such as Tween or polyethylene glycol. Thus, the compositions and their physiologically acceptable solvates may be formulated for administration by inhalation or insufflation (either through the mouth or the nose), oral, buccal, parenteral, or rectal administration.

For oral administration, the pharmaceutical preparation may be in liquid form, for example, solutions, syrups or suspensions, or may be presented as a drug product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The pharmaceutical compositions may take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well-known in the art. In a preferred embodiment, the pharmaceutical composition may take the form of a capsule or powder to be dissolved in a liquid for oral consumption. Preparations for oral administration may be suitably formulated to give controlled release of the active compound.

For buccal administration, the compositions may take the form of tablets or lozenges formulated in conventional manner.

The compounds may be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may comprise formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., comprising conventional suppository bases such as cocoa butter or other glycerides.

In addition to the formulations described previously, the compounds may also be a formulated as a sustained and/or timed release formulation. The compositions must be maintained above some minimum therapeutic dose to be effective. Such sustained and/or timed release formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt. Liposomes and emulsions are well known examples of delivery vehicles or carriers for hydrophilic drugs. Common timed and/or controlled release delivery systems include, but are not be restricted to, starches, osmotic pumps, or gelatin micro capsules.

The compositions may, if desired, be presented in a pack or dispenser device which may comprise one or more unit dosage forms comprising the active ingredient. The pack may for example comprise metal or plastic foil, such as a blister pack. The pack or dispenser device may be accompanied by instructions for administration.

4.3 Dietary Supplements Comprising *Magnoliaceae* Plant Extract

The compositions of the invention may include food compositions, beverage compositions, over the counter, and dietary supplements. The *Magnoliaceae* plant or plant extract may be added to various foods so as to be consumed simultaneously. Preferably, the *Magnoliaceae* plant extract comprises at least two compounds selected from the group consisting of magnolol, honokiol, and magnoflorine. More preferably, the *Magnoliaceae* plant extract comprises about 2% honokiol by weight of the composition. As a food additive, the *Magnoliaceae* plant or plant extracts of the invention may be used in the same manner as conventional food additives, and thus, only needs to be mixed with other components to enhance the taste. Taste enhancement includes, but is not limited to, imparting to food a refreshingness, vitality, cleanness, fineness, or bracingness to the inherent taste of the food.

It will be recognized that dietary supplements may not use the same formulation ingredients or have the same sterile and other FDA requirements as pharmaceutical compositions. The dietary supplements may be in liquid form, for example, solutions, syrups or suspensions, or may be in the form of a product for reconstitution with water or any other suitable liquid before use. Such liquid preparations may be prepared by conventional means such as a tea, health beverage, dietary shake, liquid concentrate, or liquid soluble tablet, capsule, pill, or powder such that the beverage may be prepared by dissolving the liquid soluble tablet, capsule, pill, or powder within a liquid and consuming the resulting beverage. Alternatively, the dietary supplements may take the form of tablets or capsules prepared by conventional means and optionally including other dietary supplements including vitamins, minerals, other herbal supplements, binding agents, fillers, lubricants, disintegrants, or wetting agents, as those discussed above. The tablets may be coated by methods well-known in the art. In a preferred embodiment, the dietary supplement may take the form of a capsule or powder to be dissolved in a liquid for oral consumption.

The magnitude of the dietary dose of an active ingredient in the acute or chronic management of a disorder or condition will vary with the severity of the disorder or condition to be treated and the route of administration. The dose, and perhaps the dose frequency, will also vary according to age, body weight, response, and the past medical history of the consumer or patient. Suitable dosing regimens can be readily selected by those skilled in the art with due consideration of such factors.

The amount of *Magnoliaceae* plant or plant extract in a beverage or incorporated into a food product will depend on the kind of beverage, food and the desired effect. In general, a single serving comprises an amount of about 0.1% to about 50%, preferably of about 0.5% to about 20% of the food composition. More preferably a food product comprises *Magnoliaceae* plant or plant extract in an amount of about 1% to about 10% by weight of the food composition.

Examples of food include, but are not limited to, confectionery such as sweets (candies, jellies, jams, etc.), gums, bean pastes, baked confectioneries or molded confectioneries (cookies, biscuits, etc.), steamed confectioneries, cacao or cacao products (chocolates and cocoa), frozen confectioneries (ice cream, ices, etc.), beverages (fruit juice, soft drinks, carbonated beverages), health drinks, health bars, and tea (green tea, black tea, etc.).

4.4 Dosage

The magnitude of a therapeutic or prophylactic dose of *Magnoliaceae* plant in the prevention, treatment, or management of sleeplessness, restlessness, weight gain including, but not limited to, weight gain due to stress or lack of sleep, or all three will vary with the severity of the condition of the consumer or patient to be treated and the route of administration. The dose, and dose frequency, will also vary according to the age, body weight, condition and response of the individual consumer or patient, and the particular *Magnoliaceae* plant combination used. All combinations described in the specification are encompassed as therapeutic, and it is understood that one of skill in the art would be able to determine a proper dosage of particular *Magnoliaceae* plant composition using the parameters provided in the invention.

In general, the total daily dose ranges of the *Magnoliaceae* plant for the conditions described herein are generally from about 1 mg/kg to about 140 mg/kg administered in divided doses administered parenterally, orally, or topically. A preferred total daily dose is from about 7 mg/kg to about 100 mg/kg of the *Magnoliaceae* plant composition. When a *Magnoliaceae* plant extract is used, the total daily dose ranges of the *Magnoliaceae* plant extract for the conditions described herein are generally from about 4 mg/kg to about 12.5 mg/kg administered in divided doses administered parenterally, orally, or topically. A preferred total daily dose is from about 5 mg/kg to about 11 mg/kg of the *Magnoliaceae* plant extracts.

Alternatively, the daily dose of the *Magnoliaceae* plant for the conditions described herein are generally from about 100 mg to about 800 mg, preferably from about 200 mg to 600 mg, of a 2% honokiol composition.

For example, in one embodiment, the daily dose ranges of *Magnoliaceae* plant extracts compositions described herein are generally about 7 mg per kg body weight of *Magnoliaceae* plant extracts composition. Preferably the *Magnoli-*

*aceae* plant extracts formulation of the invention is given daily until the symptoms cease, followed by two to ten additional cycles, each lasting about 60 days in duration. When the dose is administered orally, a sustained release formulation can be used so that a fairly constant level of *Magnoliaceae* plant extracts is provided over the course of treatment. As the *Magnoliaceae* plant extracts are not particularly toxic, the formulation may be administered for as long as necessary to achieve the desired therapeutic effect.

In the case where an intravenous injection or infusion composition is employed, a suitable dosage range for use is, e.g., from about 0.01 to about 150 mg per kg body weight of *Magnoliaceae* plant extracts daily.

Again, any suitable route of administration may be employed for providing the consumer or patient with an effective dosage of *Magnoliaceae* plant or plant extracts composition of this invention. Dosage forms include tablets, troches, cachet, dispersions, suspensions, solutions, capsules, gel caps, caplets, compressed tablets, sustained release devices, patches, and the like.

The dietary supplements and pharmaceutical compositions of the present invention comprise *Magnoliaceae* plant or plant extracts as the active ingredients, as well as pharmaceutically acceptable salts thereof, and may also comprise a pharmaceutically acceptable carrier, and optionally, other therapeutic ingredients.

The dietary supplements and pharmaceutical compositions include compositions suitable for oral and parenteral (including subcutaneous, intramuscular, intrathecal, intravenous, and other injectables) routes, although the most suitable route in any given case will depend on the nature and severity of the condition being treated.

In addition, the *Magnoliaceae* plant or plant extracts carrier could be delivered via charged and uncharged matrices used as drug delivery devices such as cellulose acetate membranes, also through targeted delivery systems such as liposomes attached to antibodies or specific antigens.

In practical use, *Magnoliaceae* plant or plant extracts can be combined as the active ingredient(s) in intimate admixture with a pharmaceutical carrier according to conventional pharmaceutical compounding techniques. The carrier may take a wide variety of forms depending on the form of preparation desired for administration, e.g. oral or parenteral (including tablets, capsules, powders, intravenous injections or infusions). In preparing the compositions for oral dosage form any of the usual pharmaceutical media may be employed, e.g., water, glycols, oils, alcohols, flavoring agents, preservatives, coloring agents, and the like; in the case of oral liquid preparations, e.g., suspensions, solutions, elixirs, liposomes and aerosols; starches, sugars, microcrystalline cellulose, diluents, granulating agents, lubricants, binders, disintegrating agents, and the like in the case of oral solid preparations e.g., powders, capsules, and tablets. In preparing the compositions for parenteral dosage form, such as intravenous injection or infusion, similar pharmaceutical media may be employed, e.g., water, glycols, oils, buffers, sugar, preservatives, and the like know to those skilled in the art. Examples of such parenteral compositions include, but are not limited to Dextrose 5% (w/v), normal saline or other solutions. The total dose of the *Magnoliaceae* plant extracts may be administered in a vial of intravenous fluid, e.g., ranging from about 0.7 to about 14 mg per kg body weight of *Magnoliaceae* plant extracts. The volume of dilution fluid will vary according to the total dose administered and over the length of the period of time of administration.

5. EXAMPLES

Certain embodiments of the invention, as well as certain novel and unexpected advantages of the invention, are illustrated by the following non-limiting examples.

5.1 Restful Sleep Activity

5.1.1 Materials and Methods

Using a model study with 50 volunteer participants, an extract of the invention was tested for its ability to induce restful sleep properties as discussed below.

5.1.1.1 Subjects

The study quantified consumers' perceptions and reactions to a dietary supplement containing *Magnoliaceae* extract. The study was an open-label, home usage study to test the effectiveness of dietary supplements having *Magnoliaceae* extract. The study followed 50 respondents between the age of 30 and 55 using the dietary supplement for two weeks. The typical subject had used dietary supplements within the past three months; suffered from mild anxiety or nervousness at least once in the past two months or at least six times a year; and had not taken prescription medication for the treatment of mild anxiety or nervousness in the past year. Female participants were screened to ensure that they were not pregnant or nursing an infant.

5.1.1.2 Test Materials

The sample developed and screened for sleep inducing activity was a hydroalcoholic extract from the *Magnoliaceae* family provided in a 200 mg capsule.

5.1.1.4 Procedure

All participants were asked to measure sample effectiveness by answering a series of questions directed to particular conditions. Specifically, the participants were asked to monitor whether the composition was effective to help them relax; reduce occasional nervous tension; gently soothe tension; calm the participant when feeling stressed; help control irritability; help overcome feelings of restlessness; and help the participant cope with everyday overwork and fatigue.

Participants self administered the composition in capsule form about 2–3 times during the day.

5.1.2 Results

The respondents took the capsules on an average of 2.7 per day mostly during the early morning hours before 9 a.m. or during the evening between 5 p.m. and 10 p.m. Of the subjects, 68% felt that the composition was overall effective. Of the subjects, 78% felt that the composition was highly effective in inducing a state of relaxation without feeling drowsiness. Of the subjects, 74% felt that the composition induced restful sleep and was non-sedating. Also, of the subjects 94% did not feel an upset the stomach or thought the sample had an unpleasant taste.

5.2 Weight Control

*Magnoliaceae* extracts can be tested for weight control activity by any number of means know to those skilled in the art, including, but not limited to, short term appetite control paradigms on mice using the protocol in Talpur, N. A., Echard, B. W.; Manohar, V; and Preuss, H. G.; "Influence of a combination of herbs on appetite supression and weight loss in rats," *Diabetes, Obesity & Metabolism*. 3, 3 (2001); or in Brown M.; Bing, C.; King, P.; Pickavance L; Heal, D.; and Wilding, J.; "Sibutramine reduces feeding, body fat, and improves insulin resistance in dietary-obese male winstar rats independently of hypothalamic neuropeptide Y," *British Journal of Pharmacology*. 138, 8 (2001).

It is to be understood that the present invention is not limited to the embodiments described above, but encompasses any and all embodiments within the scope of the following claims.

What is claimed is:

1. A method for treating or preventing sleeplessness in a mammal having elevated cortisol levels which comprises administering to said mammal an extract of a *Magnoliaceae* plant, said plant belonging to a genus selected from the group consisting of *Liriodendron* and *Magnolia*, said extract being administered in an amount effective to attain homeostatic cortisol levels in said mammal.

2. The method of claim 1 wherein said elevated cortisol levels of said mammal are induced by stress.

3. The method of claim 1 wherein said elevated cortisol levels of said mammal are induced by fatigue.

4. The method of claim 1 wherein the *Magnoliaceae* plant extract comprises at least two compounds selected from the group consisting of magnolol, honokiol, and magnoflorine.

5. The method according to claim 1 wherein the *Magnoliaceae* plant extract comprises about 2% of honokiol.

6. The method of claim 1, wherein said method further comprises coadministering said extract with a sleep-inducing supplement.

7. The method of claim 1 wherein said method further comprises coadministering said extract with a pharmaceutical composition for inducing sleep.

8. The method of claim 1 wherein said extract is administered to a mammal having normal cortisol levels.

9. The method of claim 1 wherein said mammal is a human.

10. The method of claim 9 wherein said human is a male.

11. The method of claim 10 wherein said human is a female.

12. A method for treating or preventing restlessness in a mammal having elevated cortisol levels which comprises administering to said mammal an extract of a *Magnoliaceae* plant, said plant belonging to a genus selected from the group consisting of *Liriodendron* and *Magnolia*, said extract being administered in an amount effective to attain homeostatic cortisol levels in said mammal.

13. The method of claim 12 wherein said elevated cortisol levels of said mammal are induced by stress.

14. The method of claim 12 wherein the *Magnoliaceae* plant extract comprises at least two compounds selected from the group consisting of magnolol, honokiol, and magnoflorine.

15. The method according to claim 12, wherein the *Magnoliaceae* plant extract comprises about 2% of honokiol.

16. The method of claim 12 wherein said extract is administered to a mammal having normal cortisol levels.

17. The method of claim 12 wherein said mammal is a human.

18. The method of claim 17 wherein said human is a male.

19. The method of claim 17 wherein said human is a female.

* * * * *

UNITED STATES PATENT AND TRADEMARK OFFICE
CERTIFICATE OF CORRECTION

PATENT NO.    : 6,814,987 B2
DATED         : November 9, 2004
INVENTOR(S)   : Martin Stogniew and Robert Garrison, Jr.

It is certified that error appears in the above-identified patent and that said Letters Patent is hereby corrected as shown below:

Title page,
Item [75], Inventors, delete "Walter Chamblis, Memphis, TN (US)".

Signed and Sealed this

Thirty-first Day of January, 2006

JON W. DUDAS
*Director of the United States Patent and Trademark Office*